(12) United States Patent
Feuerbaum (10) Patent No.: US 7,586,093 B2
(45) Date of Patent: Sep. 8, 2009

(54) APPARATUS AND METHOD FOR INSPECTING A SAMPLE OF A SPECIMEN BY MEANS OF AN ELECTRON BEAM

(75) Inventor: Hans-Peter Feuerbaum, Munich (DE)

(73) Assignee: ICT, Integrated Circuit Testing Gesellschaft fur Halbleiterpruftechnik mbH, Heimstetten (DE)

( * ) Notice: Subject to any disclaimer, the term of this patent is extended or adjusted under 35 U.S.C. 154(b) by 255 days.

(21) Appl. No.: 10/554,572

(22) PCT Filed: Apr. 26, 2004

(86) PCT No.: PCT/EP2004/004402

§ 371 (c)(1),
(2), (4) Date: Nov. 6, 2006

(87) PCT Pub. No.: WO2004/097378

PCT Pub. Date: Nov. 11, 2004

(65) Prior Publication Data

US 2007/0057182 A1 Mar. 15, 2007

(30) Foreign Application Priority Data

Apr. 28, 2003 (EP) .................................. 03009558

(51) Int. Cl.
*A61N 5/00* (2006.01)
*G21G 5/00* (2006.01)
*G01N 23/00* (2006.01)
*G21K 7/00* (2006.01)

(52) U.S. Cl. ...................... 250/311; 250/310; 250/306; 250/307; 250/492.3

(58) Field of Classification Search .................. 250/306, 250/310, 491.1, 440.11, 442.11, 441.11, 250/307, 311, 492.2, 492.3
See application file for complete search history.

(56) References Cited

U.S. PATENT DOCUMENTS 5,270,552 A   12/1993   Ohnishi et al.

(Continued)

FOREIGN PATENT DOCUMENTS

EP      0 687 897 A1   12/1995

OTHER PUBLICATIONS

William E. Vanderlinde, "STEM (scanning transmission electron microscopy) in a SEM (scanning electron microscope) for Failure Analysis and Metrology," *Proceedings from the 28th International Symposium for Testing and Failure Analysis*, Nov. 2002, Phoenix, Arizona, pp. 77-85.

(Continued)

*Primary Examiner*—Jack I Berman
*Assistant Examiner*—Brooke Purinton
(74) *Attorney, Agent, or Firm*—Patterson & Sheridan, L.L.P.

(57) ABSTRACT

The invention refers to an apparatus (10) for inspecting a sample (12) of a specimen (14) by means of an electron beam (34) comprising a vacuum chamber (18); an ion beam device (20) for generating an ion beam (22) used for etching a sample (12) from the specimen (14) within said vacuum chamber (18); an electron beam device (30) having a scanning unit (32) for scanning the electron beam (34) across said specimen (14) within said vacuum chamber (18); said electron beam device (30) having a first detector (36) positioned to detect electrons (38) that are released from the specimen (14) in a backward direction with respect to the direction of the electron beam (34); and said electron beam device (30) having a second detector (40) positioned to detect electrons (42) that are released from the sample (12) of the specimen (14) in a forward direction with respect to the direction of the electron beam (34); and separation means (50; 52) within said vacuum chamber (18) to separate the sample (12) from the specimen (14) for the inspection of the sample (12) by means of the second detector (40). With the apparatus according to the invention, it is possible to perform a transmission inspection of a sample of a specimen, e.g. a thin slice of a semiconductor wafer, at a high throughput at comparably low costs.

24 Claims, 3 Drawing Sheets

U.S. PATENT DOCUMENTS

| | | | |
|---|---|---|---|
| 5,525,806 | A | 6/1996 | Iwasaki et al. |
| 5,656,811 | A * | 8/1997 | Itoh et al. ............... 250/310 |
| 5,986,264 | A * | 11/1999 | Grunewald ............... 250/310 |
| 6,188,068 | B1 | 2/2001 | Shaapur et al. |
| 6,417,512 | B1 | 7/2002 | Suzuki |
| 6,630,667 | B1 * | 10/2003 | Wang et al. ............... 250/310 |
| 6,777,675 | B2 * | 8/2004 | Parker et al. ............... 250/310 |
| 2002/0050565 | A1 * | 5/2002 | Tokuda et al. ............... 250/310 |
| 2003/0098416 | A1 * | 5/2003 | Shemesh et al. ............ 250/310 |
| 2003/0183776 | A1 * | 10/2003 | Tomimatsu et al. .... 250/442.11 |
| 2004/0089821 | A1 * | 5/2004 | Shichi et al. ........... 250/492.21 |

OTHER PUBLICATIONS

Ludwig Reimer, "Transmitted Electron Mode," *Scanning Electron Microscopy: Physics of Image Formation and Microanalysis*, Chap. 8.4, Springer Verlag, pp. 312-314.

Edward Coyne, "A Working Method for Adapting the (SEM) Scanning Electron Microscope to Produce (STEM) Scanning Transmission Electron Microscope Images", *Proceedings from the 28$^{th}$ International Symposium for Testing and Failure Analysis*, Nov. 2002, Phoenix, Arizona, pp. 93-99.

B. Köhler and L. Bischoff, "*Entwicklung einer neuen Technologie zur Probenpräparation für die Transmissions-Elektronenmikroskopie (TEM) auf der Basis der Ionenfeinstrahlbearbeitung*" from "Wissenschaftlich-Technische Berichte", FZR-329, Aug. 2001, ISSN 1437-322X, Forschungszentrum Rossendorf.

* cited by examiner

APPARATUS AND METHOD FOR INSPECTING A SAMPLE OF A SPECIMEN BY MEANS OF AN ELECTRON BEAM

FIELD OF THE INVENTION

The invention relates to an apparatus and method for inspecting a sample of a specimen by means of an electron beam. In particular, the invention relates to an apparatus and method for inspecting a thin slice of a semiconductor wafer.

BACKGROUND OF THE INVENTION

For progress in microelectronics, it is important to have tools for inspecting microelectronical structures on a chip or wafer with ever increasing spatial resolution. At the same time, it is important to decrease the costs of such inspections in order for the industry to fabricate devices of ever increasing complexity at low costs.

A prominent tool for such inspections is the scanning electron microscope (SEM). The SEM uses a primary electron beam as a means to probe the surface structure of a given specimen. An interaction of the primary electron beam with the specimen causes electrons to be released into a backward direction with respect to the primary electron beam where they are detected by an electron detector. By scanning the primary electron beam across the specimen and determining the rate of the released electrons at each scan position, an image of the surface of the specimen with high spatial resolution is obtained. The spatial resolution of the image is essentially given by the size of the beam focus.

Due to the progressing miniaturization of integrated circuits, it has become important to study the crystal and layer structure of an integrated circuit structure below the surface of the wafer. This is usually done by inspecting a cross sectional thin slice (membrane) from the wafer or chip by means of a transmission electron microscope (TEM). With a TEM, a spatial resolution down to the atomic scale can be achieved, which is sufficient to analyze crystal structures and layers which may be only a few atomic layers thick. The TEM is characterized in that it detects electrons which have been transmitted through the specimen. Therefore, the detector of a TEM is positioned behind the specimen. Further, instead of using a scanning unit for generating an image, a TEM comprises a complex electron beam optics between the detector and the specimen to project and magnify an image of the specimen structure onto the detector. In order to capture the image of the specimen structure with high precision, the TEM detector needs to be highly segmented e.g. like a CCD.

The preparation and manipulation of a membrane of a wafer or chip for a TEM inspection represents a major complication because the use of a TEM requires that the membrane is sufficiently thin (typically 10 to 100 nm thickness) in order for the primary electrons to be transmitted through the sample. Fabrication and handling of such thin membranes is no easy task. In recent years, however, the use of focussed ion beam devices (FIB) for etching a membrane from a wafer has been established which significantly simplifies the sample preparation, see e.g. U.S. Pat. No. 6,188,068 by F. Shaapur and R. Graham, or B. Köhler and L. Bischoff *"Entwicklung einer neuen Technologie zur Probenpräparation für die Transmissions-Elektronenmikroskopie (TEM) auf der Basis der Ionenfeinstrahlbearbeitung"* from "Wissenschaftlich-Technische Berichte", FZR-329, August 2001, ISSN 1437-322X, Forschungszentrum Rossendorf.

Despite the progress in TEM sample preparation and TEM inspection, it is still complicated, expensive and time-consuming to carry out a TEM inspection because of the many steps needed for each measurement. For example, for a TEM integrated circuit failure analysis, it is required to (a) determine the position of the defect on the wafer or chip surface; this step is usually performed by an SEM inspection; (b) preparing a cross sectional membrane from the wafer at the defective position; this step is usually performed by a FIB; the FIB may be combined with a second SEM in order to observe and control the etching of the wafer; (c) moving the membrane into the TEM, and (d) inspecting the membrane by means of the TEM.

Each of the steps is time-consuming and has its own pitfalls. E.g., step (b) is highly critical because of the mechanical fragility of the very thin membrane; step (c) is critical because of a possible pollution of the membrane in the atmospheric environment during transport; and step (d) is expensive because the TEM itself is an expensive device, is difficult to operate which requires experts that can operate the TEM and evaluate the measurements. Further, to carry out the steps (a) through (d) for a TEM membrane inspection requires an SEM, a FIB or FIB/SEM system, and a TEM, which together are expensive. Further, SEM, FIB and TEM each require a high quality vacuum for operation. Providing such a vacuum each time when a wafer is taken in and out of the respective device is time-consuming.

For these reasons, inspections of cross sectional thin slices of a specimen, in particular the inspection of membranes of a wafer or chip, are expensive. Cross sectional inspections for a failure analysis of integrated circuits on a regular basis are therefore not possible.

It is therefore a first aspect of the present invention to provide an apparatus and method for inspecting a sample of a specimen which does not have the above mentioned disadvantages.

It is a further aspect of the present invention to provide an apparatus for inspecting a cross sectional slice (membrane) of a wafer in a cost- and time-saving way, to make it available in high-throughput production lines.

It is a further aspect of the present invention to provide an apparatus for inspecting a membrane which reduces wafer handling problems and exposure of the membrane to an atmospheric environment.

It is a further aspect of the present invention to provide an apparatus for inspecting a membrane of a wafer which can be integrated into existing semiconductor fabrication lines in an efficient way.

SUMMARY OF THE INVENTION

These and other problems are solved by the apparatus according to claim 1 and by the method disclosed in claim 15. Further aspects and improvements of the invention are disclosed in the description, the dependent claims and the drawings.

The present invention includes an apparatus for inspecting a sample of a specimen by means of an electron beam comprising a vacuum chamber, an ion beam device for generating an ion beam used for etching a sample from the specimen within said vacuum chamber; an electron beam device having a scanning unit for scanning the electron beam across said specimen within said vacuum chamber; said electron beam device having a first detector positioned to detect electrons that are released from the specimen in a backward direction with respect to the direction of the electron beam; said electron beam device having a second detector positioned to detect electrons that are released from the sample in a forward direction with respect to the direction of the electron beam;

and separation means within said vacuum chamber to separate the sample from the specimen for the inspection of the sample by means of the second detector.

With the apparatus according to claim 1, it is possible to inspect the surface of a specimen by means of the electron beam device and the first detector (SEM mode), to etch a sample from the specimen by means of the ion beam device (FIB mode) and to inspect the sample of the specimen by means of the second detector (transmission mode), all within the same vacuum chamber. This way, it is possible that the sample of the specimen remains in a vacuum until its inspection is finished. As a consequence, measurements of the sample are not distorted by a pollution layer which otherwise, during transport in an atmospheric environment, would have been formed on the sample. Further, with a common vacuum chamber, time-consuming venting and evacuation procedures between a SEM inspection, FIB etching and transmission mode inspection are eliminated.

Further, with the apparatus according to claim 1, no expensive TEM with its complex magnification optics and imaging detector is needed for a transmission imaging. Instead, the inspection of the sample in the transmission mode is carried out by the electron beam device in combination with the second detector. The electron beam device according to claim 1 in combination with the second detector may not achieve a spatial resolution as high as a TEM. However, depending on the electron beam spot size and the thickness of the sample, a spatial resolution of 1 nm is still achievable, which often is sufficient for a failure analysis. (see e.g. L. Reimer: "Scanning Electron Microscopy, Physics of Image Formation and Microanalysis", Chapter 8.4, Springer Verlag; E. Coyne "A working Method for adapting the (SEM) Scanning Electron Microscope to Produce (STEM) Scanning Transmission Electron Microscope Images" Proceedings from the 28$^{th}$ International Symposium for Testing and Failure Analysis, 3-7 Nov. 2002, Phoenix, Ariz.; or W. E. Vanderlinde "STEM (scanning transmission electron microscopy) in a SEM (scanning electron microscope) for Failure Analysis and Metrology", Proceedings from the 28$^{th}$ International Symposium for Testing and Failure Analysis, 3-7 Nov., 2002, Phoenix Ariz.).

In addition, even though a TEM may achieve a higher spatial resolution than a scanning transmission electron microscope, scanning of the electron beam makes it possible to create an X-ray image of the sample of the specimen by providing an additional X-ray detector which detects X-rays during the scan. The X-ray image carries information not only about the structural shape but also about the atomic material distribution in the sample of the specimen. This information can be important for many applications, in particular for an integrated circuit analysis.

Further, through the presence of the first and the second detector, it is possible to perform a high resolution imaging of the sample of the specimen with electrons released in a backward direction (i.e. secondary or backscattered electrons) in parallel to a transmission mode measurement. Due to the thin sample thickness, the spatial resolution of the "backward released electron" image is superior to the spatial resolution of the inspection on the specimen.

Further, the apparatus according to claim 1 dramatically saves costs compared to the previously known equipment needed for an inspection of a membrane of a wafer, which had to include an SEM, a FIB with an SEM and a TEM. With the apparatus according to claim 1, the same operations can be performed having only an SEM with an additional second detector and a FIB. The multiple use of the electron beam device saves considerable purchasing costs. Further, for the apparatus according to claim 1, vacuum equipment for only one vacuum chamber instead of two or three vacuum chambers is needed. In particular, the operation of an SEM and its second detector is much easier than a TEM with its sophisticated imaging beam optics and imaging detector.

The easy handling of the apparatus according to claim 1 facilitates a high degree of automation, which is especially useful in a high-throughput semiconductor fabrication line. Further, the apparatus according to the invention is characterized in that it is easily integrated into a given semiconductor processing line where SEMs are needed anyway for non-destructive inspections during the fabrication. By substituting such an SEM by the apparatus according to the invention, an inspection of membranes of wafers being processed in the production line is made available at comparably low costs. Low costs and high throughput facilitate cross sectional sample inspections in the fabrication line on a regular basis which helps to dramatically improve the quality control.

The present invention further includes a method for inspecting a sample of a specimen by means of an electron beam comprising the steps as described in claim 15, that is: a) providing an apparatus having a vacuum chamber, an ion beam device to generate an ion beam and an electron beam device to generate an electron beam; b) introducing the specimen into the vacuum chamber; c) irradiating the specimen in the vacuum chamber by means of the electron beam; d) etching the sample from the specimen in the vacuum chamber by means of the ion beam; and e) irradiating the sample of the specimen in the vacuum chamber by means of the electron beam.

With the method, it is possible to locate a defect on a wafer (SEM mode), to fabricate a membrane from the wafer (FIB mode) and inspect the membrane by means of transmitted electrons (transmission mode) with only one electron beam device and only one ion beam device. This way, a surface image and a complementary cross sectional image of a defective region of a integrated circuit can be obtained in a time and cost efficient way. In addition to the low costs, compared to previously known TEM inspection systems, the method according to claim 15 can be used to save time by carrying out the inspection cycle of the steps c) to e) of claim 15 in vacuum. This eliminates delays due to the repeated venting and evacuation procedures which are required for loading and unloading previously known SEMs, FIBs and TEMs.

BRIEF DESCRIPTION OF THE DRAWINGS

Some of the above indicated and other more detailed aspects of the invention will be described in the following description and partially illustrated with reference to the figures. Therein.

DESCRIPTION OF THE PREFERRED EMBODIMENTS

In the description of the detailed embodiments below, the numbers refer to the enclosed FIGS. 1a to 1d, 2 and 3. However, the figures only represent particular, non-limiting embodiments of the invention which only have the purpose of being illustrative examples. The description below, even though it makes reference to the figures, is to be understood in a broad sense and includes any deviation from the described embodiments which is obvious to a person skilled in the art.

Generally, the apparatus 10 according to the invention is meant to be used for the inspection of any sample 12 of a specimen 14 which is suitable for transmission microscopy inspection. Preferably, the specimen 14 is a solid substrate like, e.g., a semiconductor wafer or chip, and, preferably, the sample 12 thereof is a cross sectional thin slice of the wafer or chip. For such an inspection, the inspection of the wafer 14 with the electron beam device 30 using the first detector 36 results in an image of the surface of the wafer 14 (SEM mode), e.g. to locate a defect on the structured surface of the wafer, while an inspection of the cross sectional thin slice 12 with the electron beam device 30 using the second detector 40 results in an image of the cross sectional structure of the wafer 14 (transmission mode). For the sake of simplicity, below, without being limited to such samples, the cross sectional thin slice 12 will be named "membrane" because of its elasticity and its fairly thin sheet-like shape.

Preferably, the membrane 12 is fabricated from the wafer 14 in a region where the wafer has been inspected by a previous electron beam surface inspection with the first detector 36. This way, the image obtained from the membrane and the image obtained from the wafer surface can be combined to a have complementary information of that region of the wafer. Preferably, the membrane has a thickness in the range of 5 to 500 nm and even more preferred, in the range of 10 nm to 100 nm. This way, the membrane 12 can be inspected by the electron beam device by means of the second detector 40 (transmission mode) at typical SEM electron beam energies of 5 to 50 keV (typically, energies up to 30 keV are used, but some manufacturers offer devices with 50 keV).

The vacuum chamber according to the invention is intended to provide a continuous vacuum during the irradiation of the wafer 14 by means of the electron beam device 30 (SEM mode), during the etching the membrane 12 from the wafer 14 by means of the ion beam device 20 (FIB mode) and during the irradiation of the membrane 12 by means of the electron beam device 30 (transmission mode). Preferably, the vacuum is maintained during the time between the three operational modes. In this case, the inspection of the membrane 12 and the wafer 14 is carried out without any of the two having to be in contact with the external environment. This greatly improves the reliability of the measurements.

Typically, the vacuum chamber is made to provide a vacuum in the region of the specimen which is better than $10^{-3}$ mbar, preferably better than $10^{-5}$ mbar. The better the vacuum, the better the imaging performance of the electron beam device 30 and the less the pollution of the membrane 12. Further, preferably, the vacuum chamber is connected with the ion beam device 20 and/or electron beam device 30 in order to provide a hermetic vacuum for the electron beam 34 and the ion beam 22 on their way to from their respective beam sources to the common vacuum chamber 18.

The ion beam device 20 is used to generate an ion beam 22 for etching a sample 12 from the specimen 14. Severing a sample 12 from a specimen 14 by means of an ion beam 22 has become a standard procedure (see e.g. U.S. Pat. No. 6,188,068 B1, column 3, line 49 to column 5, line 12). The focussed ion beam of the focussed ion beam device (FIB), as described in U.S. Pat. No. 6,188,068, is used to remove wafer material with high lateral spatial resolution in order to "chisel" a thin cross sectional membrane from the wafer. Preferably, the ion beam device 20 according to the invention is equipped with a mechanism, e.g. an ion beam deflector, to adjust the landing angle on the specimen. This greatly improves the flexibility for using the ion beam as a knife that shapes the membrane and cuts it off from the wafer in a desired shape. Alternatively, the specimen holder 50, which holds the specimen or wafer, is tiltably connected underneath the ion beam device in order to provide adjustable landing angles for the ion beam 22 on the wafer to chisel the membrane 12 from the wafer 14. Preferably, the ion beam source 56 generates an Ga-ion beam.

The electron beam device 30 according to the invention preferably comprises at least one electron beam source 54 to generate an electron beam 34. The electron beam source 54 may be any of the electron beam sources usually used for electron microscopes, e.g. a thermionic tungsten hairpin gun, or one of the many types of field emission electron guns known in the art. Preferably, the electron beam device 30 includes beam optical components to focus the electron beam onto the specimen 14 in order to increase the spatial resolution for both the SEM-inspection mode and the transmission mode. The electron beam device 30 further, preferably, includes at least one anode to accelerate the electrons of the electron beam 34 to a predetermined energy and/or to define the landing energy on the specimen. For typical SEM applications on a silicon wafer, the landing energy is in the range of 100 eV to 30 keV. Also, preferably, the electron beam device 30 includes a focussing lens 33 to focus the electron beam 34 onto the specimen 14 or onto the sample 12 of the specimen 14 with a spot size down to 1 nm.

The electron beam device 30 further includes a scanning unit 32 for scanning the electron beam 34 across the specimen 14 and/or the sample 12 of the specimen 14. This way, the electron beam device 30 can be operated as an SEM to inspect the surface of the specimen using the first detector 36 to detect the electrons 38 that are released from the specimen 14 in a backward direction with respect to the direction of the electron beam 34. Further, with the scanning unit 32, the electron beam device 30 can be operated as a scanning transmission electron microscope to inspect the sample 12 of the specimen 14 in the transmission mode by using the second detector 40. The second detector is meant to detect the electrons 42 that are released from the specimen 14 in a forward direction with respect to the direction of the electron beam 34.

The first detector 36 is meant to cover at least some of the area of the upper hemisphere of the specimen 14. The term "upper hemisphere" refers to the hemisphere into which electrons 38 are directed which are released from the specimen 14 in a backward direction with respect to the electron beam 34. The first detector 36 may be enclosed within the electron beam column 31 as shown in the FIGS. 1a) to 1d); however it is also possible to position the first detector 36 outside of the emitter beam column 31, e.g. at the side of the electron beam column 31 for backward electrons 38 detection.

The size and design of the first detector 36 depends on the design of the electron beam device 30, in particular on the available space and the electric field distribution in the electron beam region. In the FIGS. 1a to 1d, the first detector 36 surrounds the electron beam axis with a circular symmetry in order to detect backwards directed electrons 38 which have entered the electron beam device 30 through the focussing lens 33. Preferably, the first detector 36 is a semiconductor detector, or a scintillation-photomultiplier detector (Everhart-Thornley detector). Both detectors are preferably capable of detecting secondary electrons having an energy of typically 0 to 50 eV, and backscattered electrons having an energy up to the full primary electron beam energy.

The second detector 40 is meant to cover at least some area of the lower hemisphere of the sample 12 of the specimen 14.

The term "lower hemisphere" refers to the hemisphere into which electrons 42, which are released from the sample 12 in a forward direction with respect to the electron beam 34, are directed. The size and design of the second detector 40 can be quite freely chosen, since below the sample there is more space and fewer electric field constraints for the second detector. However, the larger the area of the lower hemisphere covered by the second detector, the better the signal-to-noise ratio of the transmission image.

Preferably, the first detector 36 and/or the second detector 40 are essentially non-imaging detectors, i.e. detectors which are not segmented to obtain a pixel image. Rather, it is preferred that first detector 36 and/or the second detector 40 are each one-channel detectors, which are significantly easier to operate than an imaging detector like, e.g. a CCD or any other multi-pixel detector. An imaging detector is not required for the apparatus according to the invention since the imaging is preferably performed by scanning the electron beam across the specimen or the sample of the specimen.

There are several options regarding the type of detector to take as second detector 40. In one preferred embodiment of the invention, the second detector 40 is a semiconductor detector. In another preferred embodiment, the second detector 40 is a Everhart-Thornley detector. In a third preferred embodiment, the second detector 40 is a scintillator detector using a photomultiplier to amplify the scintillator signal. In this case, preferably, a light guide is used to transfer the scintillator signal to the photomultiplier.

Further, it is preferred that the distance between the focussing lens 33 and the second detector 40 is smaller than 10 cm and even more preferred smaller than 5 cm. A close distance of the second detector 40 to the focussing lens 33 may be used to have the sample 12 close up to the second detector 40. This makes it easier to detect a large solid angle of the "lower hemisphere" with a small detector area.

The apparatus according to the invention further includes separation means 50, 52 for separating the sample 12 from the specimen 14. Preferably, the separation means 50, 52 includes a specimen holder 50 to hold the specimen 14. It is further preferred that the specimen holder 50 is capable of moving the specimen from the inspection position below the electron beam device 30 to the etching position below the ion beam device 20, and retour. This way, the specimen holder 50 can be used to position the specimen 14 for the surface inspection by the electron beam device (SEM mode) as well as for the ion beam treatment (FIB mode) for the preparation of a sample from the specimen. In the case that the specimen 14 is a semiconductor wafer or a chip, the specimen holder 50 may be a movable wafer chuck.

Preferably, the specimen holder 50 also includes some mechanical means to tilt the specimen with respect to the ion beam axis. This way, the landing angle of the ion beam 22 onto the specimen is adjustable to "chisel" a desired sample from the specimen with higher flexibility.

Preferably, the separation means 50, 52 further include a sample holder 52 to hold the sample 12. Preferably, the sample holder 52 is movable in order to pick up the sample 12 from the specimen and move it away from the specimen 14. Preferably, the sample holder 52 is capable of moving the sample to the electron beam device 30 for the inspection in transmission mode, i.e. by means of the second detector 40. It is further preferred that the sample holder 52 moves the sample 12 to the electron beam device 30 in a vacuum. This way, the sample 12 is not exposed to the atmosphere.

The particular shape and functionality of the sample holder 52 depends on the application and the kind of specimen. The technology to pick up and move a thin membrane is known in the art, e.g. U.S. Pat. No. 6,188,068 B1 discloses an example of such a sample holder in column 5, lines 12 to 62, where a sample holder with a glass tip is used to pick up a membrane from a wafer to carry it to a TEM for TEM inspections. A similar sample holder 52 can be used for the present invention if the specimen 14 is a wafer and the sample 12 is a membrane (see FIG. 1a to 1d). In this case the sample holder 52 is designed to carry and position the sample into the electron beam 34 of the electron beam device 30.

As an alternative, it is preferred that the apparatus 10 includes a support structure which is formed and positioned to hold the sample 12 into the electron beam 34 of the electron beam device 30. In this case, the sample holder 52 is to move the sample 12 to the sample holder to lay it thereon. Such a procedure provides a good stability of the specimen during inspection in the transmission mode. The support structure preferably holds the sample 12 between the focussing lens 33 and the second detector 40. Further, the support structure is preferably shaped in a way that it leaves a free passage for the electrons 42 released from the sample 12 in a forward direction to the second detector 40.

Preferably, the electron beam column 31 of the electron beam device 30 is essentially in parallel to the ion beam column 21 of the ion beam device 20. In this way, the electron beam 34 and the ion beam 22 can be made to have the same landing angle on the specimen 14 in order to inspect or etch the specimen. However, it is also preferred that the electron beam device 30 has a tilting mechanism in order to inspect the specimen 14 under different landing angles. Similarly, it is also preferred for the ion beam device 30 to have a tilting mechanism in order to etch the specimen at different angles. A tiltable ion beam device 20 provides more flexibilty to etch a membrane or any other sample 12 from a given specimen 14 in any desired shape. In addition, or alternatively, the ion beam device 30 is provided with beam optical components, e.g. a beam deflector or a beam shifter, to move the ion beam 22 across the specimen 14 at various angles to obtain a desired sample 12 from the specimen 14.

Preferably, the sample holder 52 and/or the support structure are made to be electrically connectable to a DC voltage source V1 in order to be able to adjust the landing energy of the electron beam 34 on the sample 12 of the specimen. This way, the electron beam device 30 can be operated at higher landing energies during the transmission mode than without the first voltage source V1. During the transmission mode, a higher energy is preferred for a higher spatial resolution. Typically, the DC voltage source V1 is capable of providing a voltage of up to 10 keV and preferably up to 50 keV to the sample 12. In the SEM mode, the landing energy on the specimen 12 is preferably between 5 keV to 50 keV or, more preferred, between 0.1 to 30 keV.

FIG. 1a to 1d illustrate a preferred method for inspecting a sample of a specimen according to the invention. In the figures, the specimen 14 is a silicon wafer having an integrated circuit ingrained. The apparatus 10 is preferably integrated in a integrated circuit production line.

FIG. 1a to 1d disclose an electron beam device 30 with an electron beam column 31 having an electron beam source 54, a scanning unit 32 to deflect the electron beam 34 across the wafer 14, a focussing lens to focus the electron beam 34 down to a focus spot size of less than 10 nm. The electron beam device 30 further includes an electron detector 36 (first detector) to detect the electrons 38 which are released backwards into the upper hemisphere due to an interaction of the electron beam 34 with the wafer 14.

Figure 1A:
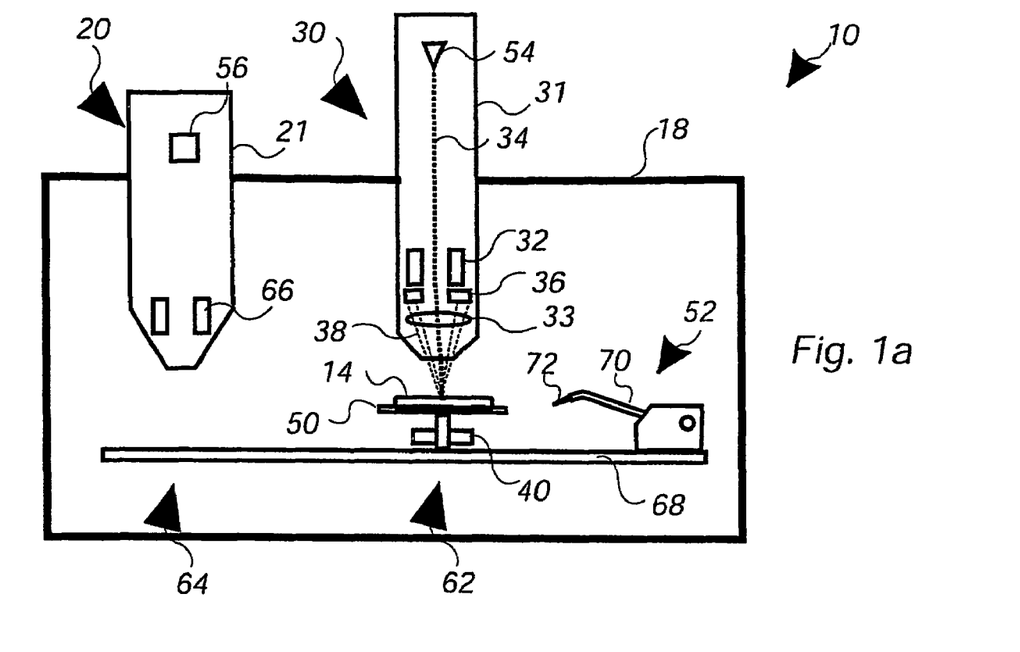
FIG. 1a to 1d disclose a first embodiment of the invention and steps for the method according to the invention.

FIG. 1a further discloses an ion beam device 20, which in FIG. 1a is a focussed ion beam device (FIB). The FIB 20 includes a Ga-ion beam source 56 and an ion beam scanning unit 66 to scan the ion beam 22 across the wafer 14 to etch a membrane 12 out of the wafer. The focus of the ion beam 22 on the wafer 14 is typically 5 to 100 nm wide. With the ion beam 22, the FIB 20 is capable of etching a membrane 12, which has to be only a few tens of nanometers thick, out of the wafer 14. The ion beam column 21 of the FIB 20 and the electron beam column 31 of the electron beam device 30 are oriented parallel to each other.

FIG. 1*a* further discloses a stage 68 on whose surface the specimen holder 50 can be moved from the inspection position 62 to the etching position 64. The stage 68 also carries the sample holder 52 which can be moved along the stage surface. The sample holder 52 has a handling arm 70 to move the tip 72 for picking up and positioning the membrane 12 at a desired position.

Stage 68, sample holder 52 specimen holder 50 and the second detector 40 (which in FIG. 1*a* is partially covered by specimen holder 50) are all enclosed by the vacuum chamber 18 in order to provide a vacuum better than $10^{-5}$ mbar. The high vacuum is necessary to minimize electron beam spreading. The common vacuum chamber 18 makes it possible that the apparatus can be operated in the SEM mode, the FIB mode or the transmission mode without ever having to break the vacuum when switching from one mode to the other. This way, the membrane 12 is never exposed to environmental pollution during the inspection procedure.

FIG. 1*a* shows the apparatus 10 during SEM mode operation, i.e. the wafer 14 is being scanned by the electron beam 34 using the scanning unit 32 while the FIB 20 is switched off. The landing energy of the electron beam 34 on the wafer 14 is 0.1 to 30 keV. The electron beam 34 impinges on the wafer 14 because of which electrons 38 are released in a backward direction. The first detector 36, which in this embodiment is a scintillation detector, detects and counts the number of backwards directed electrons 38 for each scanning position. This way, an image of the surface structure of the wafer is generated with a spatial resolution of close to 1 nm. The image of the surface of the wafer 14 is used to determine whether and which region of interest should now be inspected in the transmission mode.

In the case that no region of interest for a transmission mode inspection is found on the wafer, the wafer 14 is forwarded to the next processing unit of the semiconductor production line for completing the processing. However, in the case that the SEM image of the wafer indicates a region of interest for further inspection in the transmission mode, the specimen holder 50 is moved on the stage 68 from the inspection position 62 to the etching position 64 in order to start the FIB mode to etch a membrane 12 from the wafer 14. To etch the membrane at the determined region of interest of the wafer 14, it is important that a communication unit (not shown) communicates the coordinates of the region of interest as measured by the electron beam device in the SEM mode to the specimen holder 14 and/or FIB. This way, the specimen holder 50 can be moved into the correct etching position 64 in order to etch the wafer 14 at the position where the region of interest is.

Figure 1B:
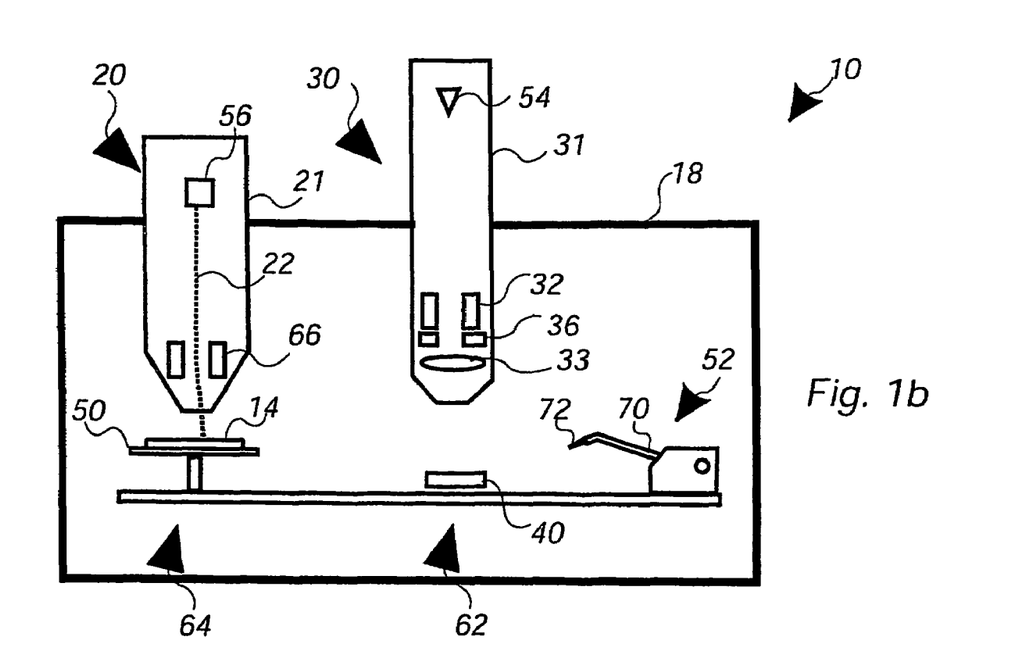

FIG. 1*b* shows the apparatus of FIG. 1*a* during the FIB mode operation. In the FIB mode, the electron beam device 30 is switched off and the FIB 30 generates an ion beam 22 to etch the membrane 12 out of the wafer 14 by scanning the ion beam in the region of interest. The method of etching a membrane 12 from a wafer 14 by means of a FIB ion beam has been discussed earlier and is known in the art.

Figure 1C:
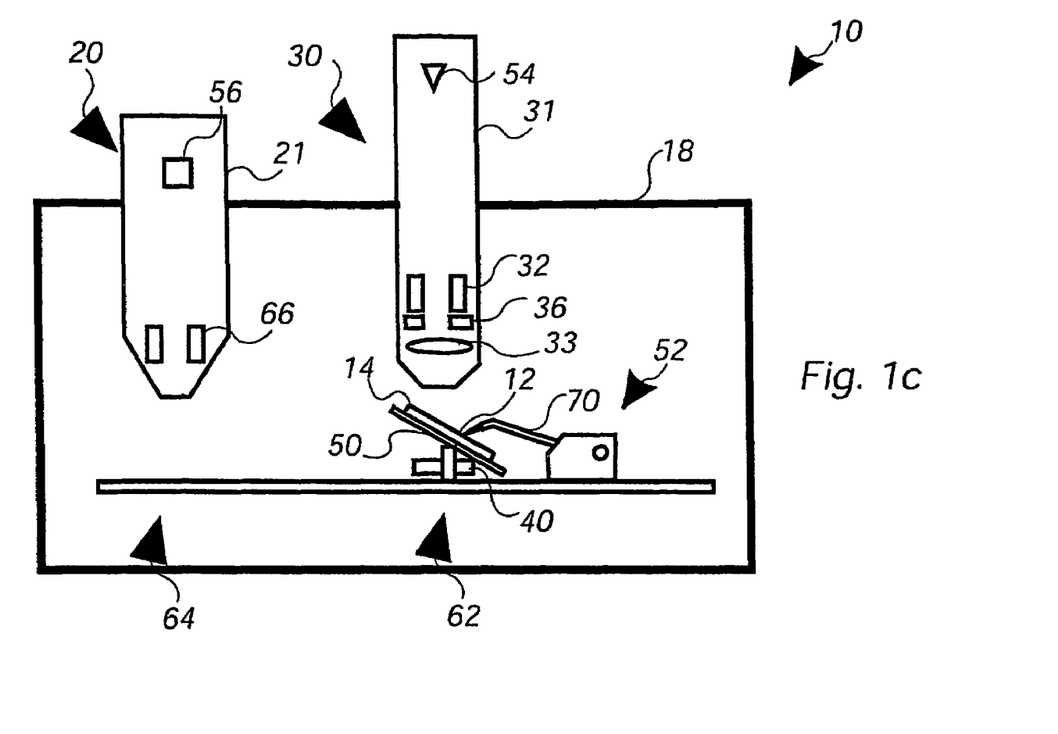

Once the membrane 12 has been etched, the specimen holder 50 with the etched wafer 14 and the membrane 12 still lying on it is moved back into the inspection position 62. There, the specimen holder 50 is tilted in order to allow for an easy extraction of the membrane 12 from the wafer 14. During this process, the electron beam device 30 can help to determine the exact position of the membrane 12 within the wafer 14. With the information of the membrane position, the sample holder 52 is moved on the stage 68 towards the wafer 14 to pick up and lift the membrane 12 away from the wafer 14. The picking of the membrane 12 is performed by means of an electrostatic force generated between the tip 72 of the sample holder 52 and the membrane 12. FIG. 1*c* illustrates the scenario at the moment when the tip 72 of the specimen holder 52 comes into contact with the membrane 12 on the wafer 14.

Once the membrane 12 has been lifted by the arm 70 of the sample holder 52, the specimen holder 50 is moved away from the inspection position 62 to make space for the inspection of the membrane 12 in the transmission mode. Then, the membrane 12 is positioned by the sample holder 52 between the focussing lens 33 and the second detector 40 for the inspection in the transmission mode.

Figure 1D:
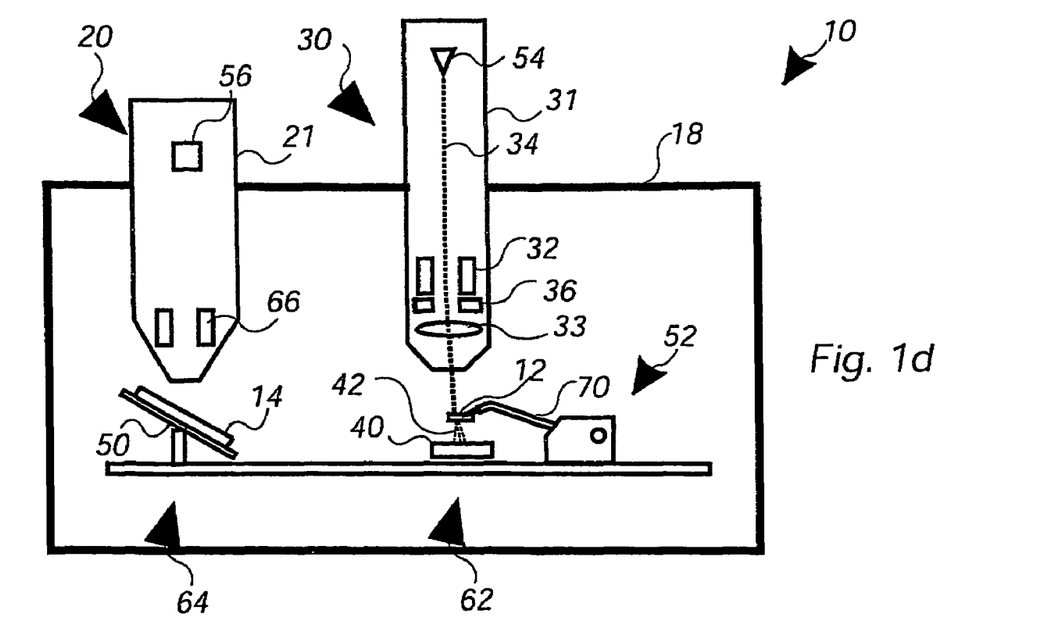

FIG. 1*d* illustrates the scenario during the inspection of the membrane 12 in the transmission mode. The second detector 40, a scintillation detector, is used to detect the electrons 42 which have been released from the membrane 12 in a forward direction with respect to the electron beam 34 while the electron beam 34 is scanned across the membrane 12. By evaluating the electron signal of the scintillation detector 40 with respect to the according scanning position, a transmission image of the membrane is generated. Even though the spatial resolution of such a scanning image may not be sufficient to reveal the crystal structure of the membrane, the spatial resolution is usually high enough to image very thin layers and details of interface regions between the layers.

It should be mentioned that during the transmission mode it is also possible to detect electrons 38 which are released from the membrane 12 in a backward direction with respect to the electron beam 34 by means of the first detector 36. The image generated by the first detector 36 can help to obtain complementary information about the surface of the membrane (which corresponds to a cross section of the wafer from which the membrane has been formed).

Figure 2:
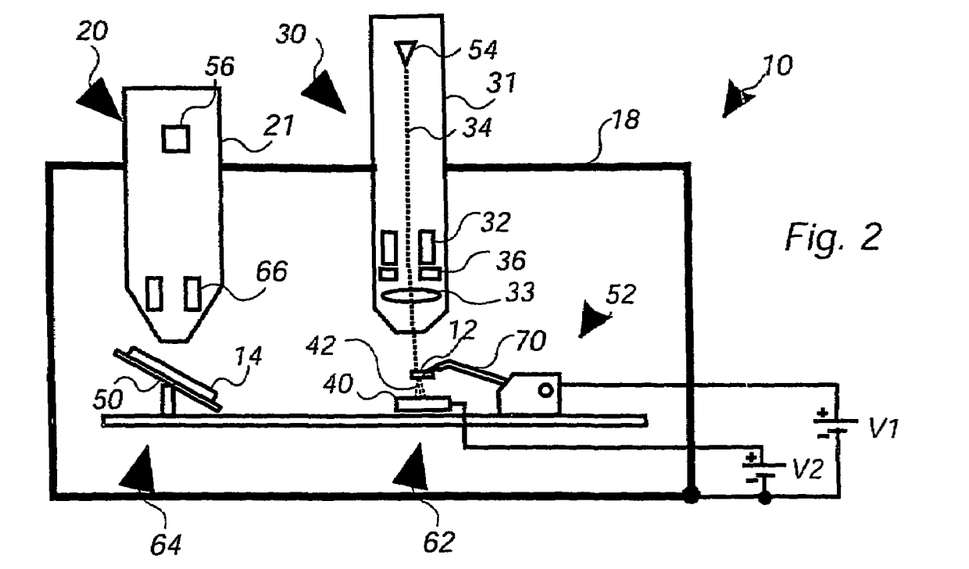
FIG. 2 discloses a second embodiment according to the invention with two additional voltage sources to increase the beam transmission energy.

FIG. 2 illustrates the same apparatus like in FIG. 1*a* to 1*d*, with the difference that a first voltage of the first voltage source V1 and a second voltage of the second voltage source V2 are applied between the sample holder 52 and vacuum chamber 18, and the scintillation detector 40 and vacuum chamber, respectively. The first voltage source V1 is mainly used in the transmission mode to apply a positive voltage to the membrane 12 in order to increase the transmission energy of the electrons of the electron beam 34 when they pass through the membrane 12. With a higher transmission energy, the spatial resolution of the transmission mode image can be increased to see even more details of the membrane structure.

In the SEM mode, the voltage of the first voltage source V1 is usually decreased in order to make sure that low energy secondary electrons can reach the first detector 36. A low voltage of the first voltage source V1 also keeps the landing energy low to obtain a higher spatial resolution in the SEM mode.

The second voltage source V2 is used to adjust the voltage of the second detector 40 to make sure that the transmitted electrons 42 have enough energy to reach the detector even when the membrane is lifted to a more positive potential.

Figure 3:
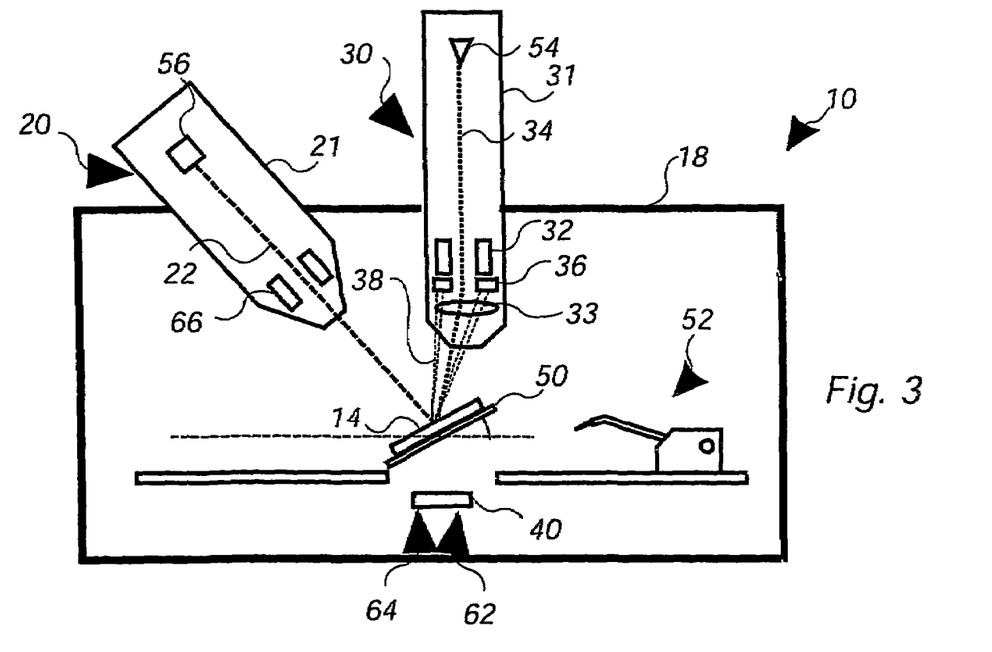
FIG. 3 discloses a third embodiment according to the invention where the ion beam device and the electron beam device are oriented to each other at an angle to have a common focussing position on the specimen.

FIG. 3 illustrates a further embodiment of the invention. The apparatus 10 of FIG. 3 is the same as the apparatus 10 of FIG. 1*a* to 1*d*, with the difference that the FIB 20 is tilted with respect to the electron beam device 30. The tilting angle of the FIB 20 is such that the ion beam 22 and the electron beam 34 can be directed onto the same region on a wafer 14. This way, it is possible to inspect the wafer 14 during the etching of the wafer 12 by means of the FIB 20, i.e. SEM mode and FIB mode can be carried out at the same time. In this case, it is not necessary to move the specimen holder 50 to the FIB after inspection in the SEM mode. This might help to increase the precision for etching the membrane 12 at the desired region of interest.

The invention claimed is:

1. An apparatus for inspecting a sample of a specimen by means of an electron beam comprising:
   a vacuum chamber;
   an ion beam device for generating an ion beam for etching a sample from the specimen within said vacuum chamber;
   an electron beam device having a scanning unit for scanning the electron beam across said specimen within said vacuum chamber, the electron beam device having a first detector positioned to detect electrons that are released from the specimen in a backward direction with respect to the direction of the electron beam and a second detector positioned to detect electrons that are released from the sample of the specimen in a forward direction with respect to the direction of the electron beam; and
   separation means within the vacuum chamber to separate the sample from the specimen for inspection of the sample by means of the second detector.

2. The apparatus of claim 1, wherein the electron beam device includes a focusing lens to focus the electron beam onto at least one of the specimen and the sample.

3. The apparatus of claim 1, wherein the separation means includes a specimen holder to hold the specimen.

4. The apparatus of claim 3, wherein the specimen holder is capable of moving the specimen away from an inspection position.

5. The apparatus of claim 3, wherein the specimen holder is capable of tilting the specimen with respect to the electron beam.

6. The apparatus of claim 1, wherein the separation means includes a sample holder to hold the sample.

7. The apparatus of claim 6, wherein the sample holder is capable of holding the sample by means of at least one of an electrostatic force and a capillary force.

8. The apparatus of claim 6, wherein the sample holder is capable of moving the sample into an inspection position.

9. The apparatus of claim 1, further comprising:
   a support structure positioned to hold the sample at a position between the scanning unit and the second detector.

10. The apparatus of claim 1, wherein the electron beam device comprises an electron beam column.

11. The apparatus of claim 10, wherein the electron beam column is substantially parallel to the ion beam column.

12. The apparatus of claim 10, wherein the electron beam column is connected to a tilting mechanism to tilt the electron beam column with respect to the ion beam column.

13. The apparatus of claim 10, wherein the ion beam column has optical components to change the landing angle of the ion beam on the specimen.

14. The apparatus of claim 1, wherein the sample holder is connectable to a voltage source to adjust the landing energy of the electron beam on the sample.

15. The apparatus of claim 1, wherein at least one of the first detector and the second detector utilizes a scintillator and a light guide.

16. The apparatus of claim 1, wherein at least one of the first detector and the second detector is a non-imaging detector.

17. The apparatus of claim 2, wherein the distance between the focusing lens and the second detector is less than 50 cm.

18. A method for inspecting a sample of a specimen by means of an electron beam comprising:
   a) providing an apparatus having a vacuum chamber, an ion beam device to generate an ion beam and an electron beam device to generate an electron beam;
   b) introducing the specimen into the vacuum chamber;
   c) irradiating the specimen in the vacuum chamber by means of the electron beam while detecting electrons released from the specimen in a backward direction with respect to the direction of the electron beam;
   d) etching the sample out of the specimen in the vacuum chamber by means of the ion beam and separating the specimen and the sample by separating means comprising a specimen holder and a sample holder; and
   e) irradiating the sample of the specimen in the vacuum chamber by means of the electron beam while detecting electrons released from the sample in a forward direction with respect to the direction of the electron beam.

19. The method of claim 18, wherein during step e), the electron beam is scanned across the sample.

20. The method of claim 18, wherein during steps c) to e), a vacuum is maintained in the vacuum chamber.

21. The method of claim 18, wherein at least one of the sample holder and the specimen holder is moved to separate the sample from the specimen.

22. The method of claim 18, wherein the sample holder is moved to position the sample into the electron beam.

23. The method of claim 18, wherein the sample is positioned by the sample holder under vacuum conditions.

24. The method of claim 18, wherein the sample holder holds the sample by means of at least one of an electrostatic force and a capillary force.

* * * * *